(12) United States Patent
Barth et al.

(10) Patent No.: US 6,228,069 B1
(45) Date of Patent: May 8, 2001

(54) NEEDLELESS ACCESS DEVICE

(75) Inventors: Steve C. Barth, McHenry, IL (US); Ralph L. Davis, Genoa City, WI (US)

(73) Assignee: Filtertek Inc., Hebron, IL (US)

( * ) Notice: Subject to any disclaimer, the term of this patent is extended or adjusted under 35 U.S.C. 154(b) by 0 days.

(21) Appl. No.: 09/286,280

(22) Filed: Apr. 5, 1999

(51) Int. Cl.[7] ..................................................... A61M 5/00
(52) U.S. Cl. ............................................. 604/249; 604/905
(58) Field of Search .................................. 604/246, 249, 604/247, 256, 905

(56) References Cited

U.S. PATENT DOCUMENTS

| | | |
|---|---|---|
| 3,570,484 | 3/1971 | Steer . |
| 3,831,629 | 8/1974 | Mackal et al. . |
| 3,965,910 | 6/1976 | Fischer . |
| 4,429,856 | 2/1984 | Jackson . |
| 4,668,215 | 5/1987 | Allgood . |
| 4,991,820 | 2/1991 | Kohn et al. . |
| 5,006,114 | 4/1991 | Rogers et al. . |
| 5,049,128 | 9/1991 | Duquette . |
| 5,147,333 | 9/1992 | Raines . |
| 5,184,652 | 2/1993 | Fan . |
| 5,201,725 | 4/1993 | Kling . |
| 5,242,432 | 9/1993 | DeFrank . |
| 5,279,579 | 1/1994 | D'Amico . |
| 5,284,475 | 2/1994 | Mackal . |
| 5,347,992 | 9/1994 | Pearlman et al. . |
| 5,353,837 | 10/1994 | Faust . |
| 5,439,451 | 8/1995 | Collinson et al. . |

*Primary Examiner*—Anhtuan T. Nguyen
*Assistant Examiner*—Jeremy Thissell
(74) *Attorney, Agent, or Firm*—Brinks Hofer Gilson & Lione

(57) ABSTRACT

A needleless access device includes a housing having a fluid pathway and an inner chamber. A biased plunger is disposed within the inner chamber and movable between a first position and a second position, and a main seal seals the inner chamber from the fluid pathway. A vent between the inner chamber and the outside of the housing allows air to pass out of and into the inner chamber when the plunger is moved between the first and the second positions.

20 Claims, 8 Drawing Sheets

FIG. 2
FIG. 3
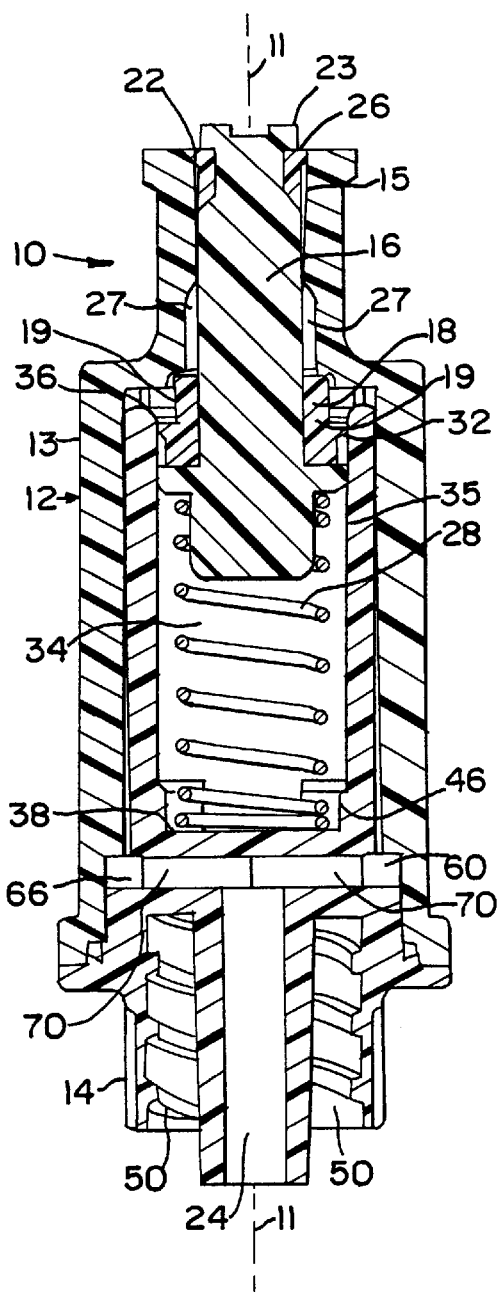
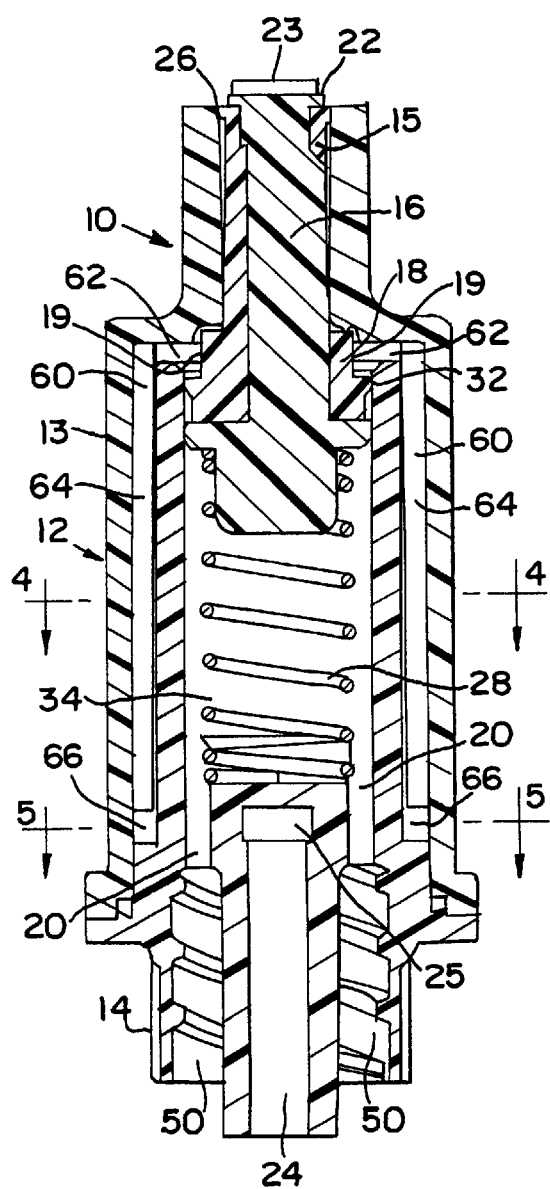

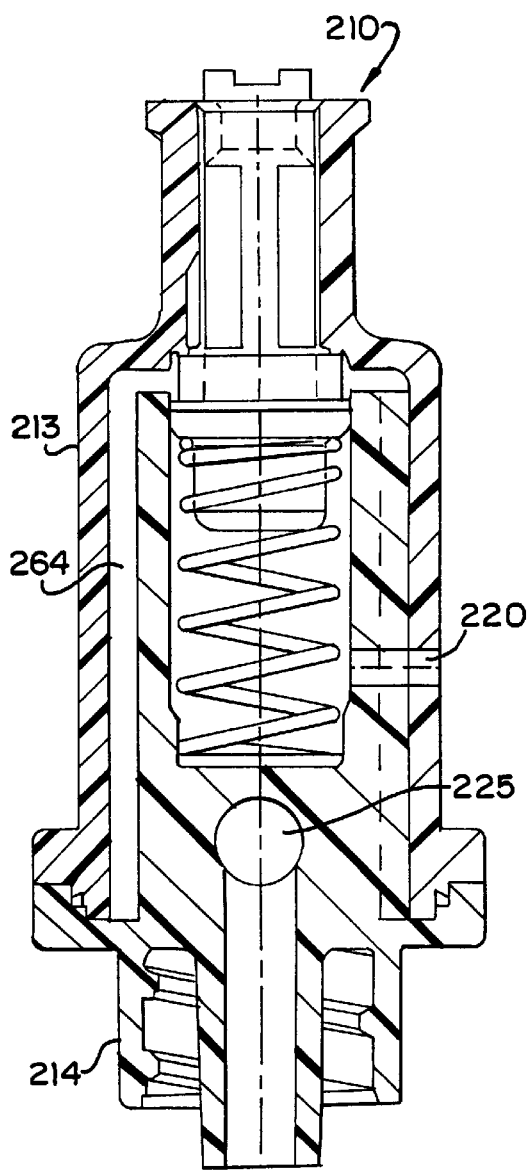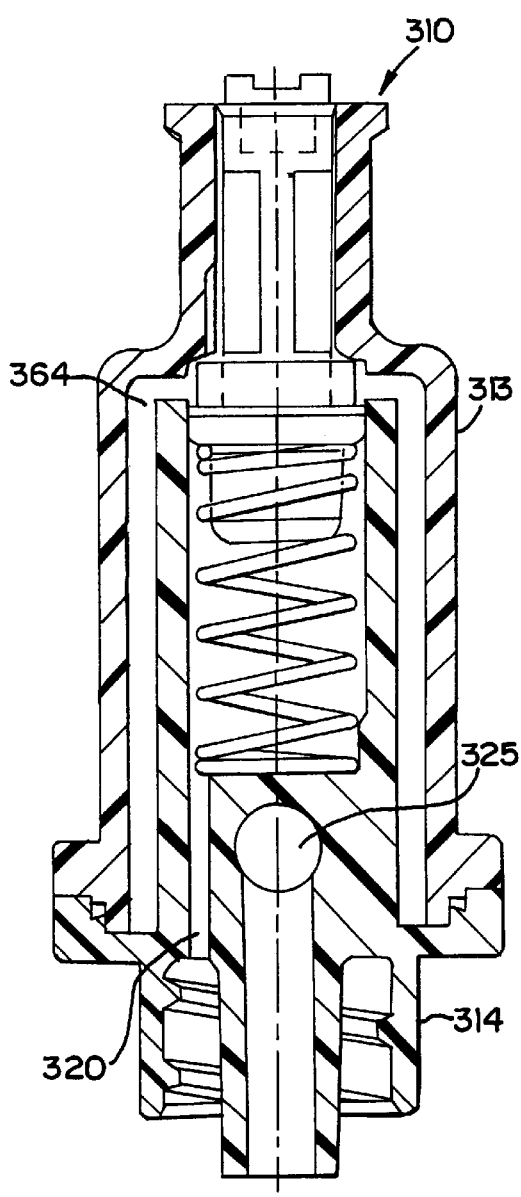

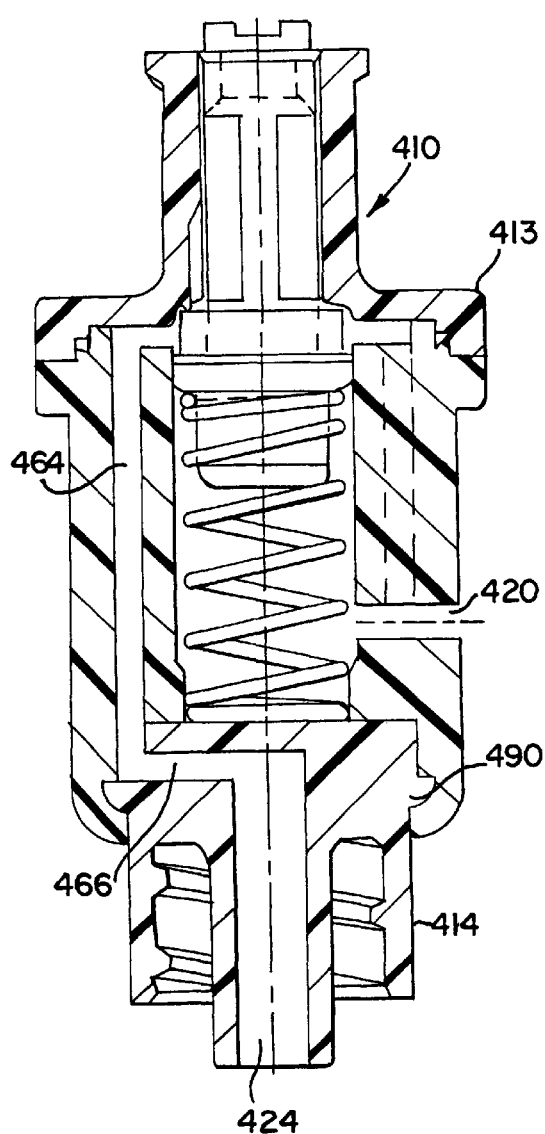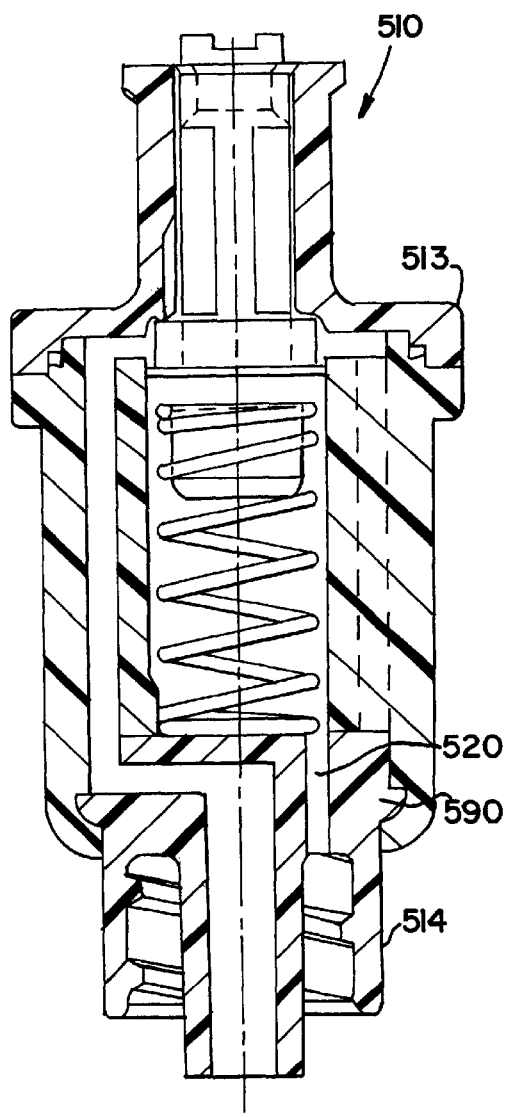

NEEDLELESS ACCESS DEVICE

BACKGROUND OF THE INVENTION

This invention relates to a needleless access device for use with liquid flow and administrative apparatus for medical purposes.

The use of hypodermic needles to inject or withdraw fluids in medical applications has been standard practice for a number of years. Even where a patient already has an IV tubing set connected to a vein, hypodermic needles are frequently used to inject fluids into the IV tubing. Often a "Y connector" with a septum is provided in the tubing set for this very purpose. The needle is used to puncture the septum to administer the drug or other fluid, and the septum then sufficiently seals the opening to prevent airborne bacteria from entering the system. Septums are also common on drug vials, where the needle is inserted to withdraw a quantity of the drug.

The widespread use of hypodermic needles leads to numerous needle-stick accidents. These are not only painful, but if the needle is contaminated, could cause serious disease or complications in the needle-stick victim.

To prevent such accidents, needleless access devices have been designed. These devices typically include a cap having an inlet opening and a body with an outlet opening. In some instances, the devices are provided with a piston that, in its normally closed position, seals the inlet opening of the device to prevent bacterial contamination and maintain sterility.

U.S. Pat. No. 5,439,451 discloses a Capless Medical Backcheck Valve for allowing liquid flow into an IV line. The backcheck valve includes a flexible elastomeric piston that has a flexible tubular wall. The use of such a flexible piston in a needleless access device tends to increase the interior hold-up volume within the device. Further, the flexible tubular wall may tend to impede fluid flow. In addition, the material required to make a flexible piston may require lubricants to function properly.

In some instances, blood and possibly other fluids may enter a needleless device through the outlet after the device has been used to administer fluid into IV tubing. This phenomenon is commonly referred to as reflux.

There is thus a desire for a needleless medical system, where a fluid can be injected or aspirated with minimal reflux, while minimizing hold-up volume, allowing unimpeded fluid flow and requiring no additional lubricants to function properly.

SUMMARY OF THE INVENTION

A needleless access device has been invented which avoids reflux while minimizing hold-up volume, allows unimpeded fluid flow and requires no additional lubricants to function properly. The device comprises a housing having a fluid pathway and an inner chamber; a biased plunger disposed within the inner chamber and movable between a first position and a second position; a main seal sealing the inner chamber from the fluid pathway; and a vent between the inner chamber and the outside of the housing to allow air to pass out of and into the inner chamber when the plunger is moved between the first and second positions.

BRIEF DESCRIPTION OF THE DRAWINGS

FIG. 2 is a cross-sectional view taken along line 2—2 of FIG. 4.

FIG. 3 is a cross-sectional view taken along line 3—3 of FIG. 4.

FIG. 4 is a cross-sectional view taken along 4—4 of FIG. 3.

FIG. 5 is a cross-sectional view taken along 5—5 of FIG. 3.

FIG. 10 is a cross-sectional view of a third embodiment of the present invention.

FIG. 11 is a cross-sectional view of a fourth embodiment of the present invention.

FIG. 12 is a cross-sectional view of a fifth embodiment of the present invention.

FIG. 13 is a cross-sectional view of a sixth embodiment of the present invention.

DETAILED DESCRIPTION OF THE DRAWINGS AND PREFERRED EMBODIMENTS OF THE INVENTION

Figure 1:
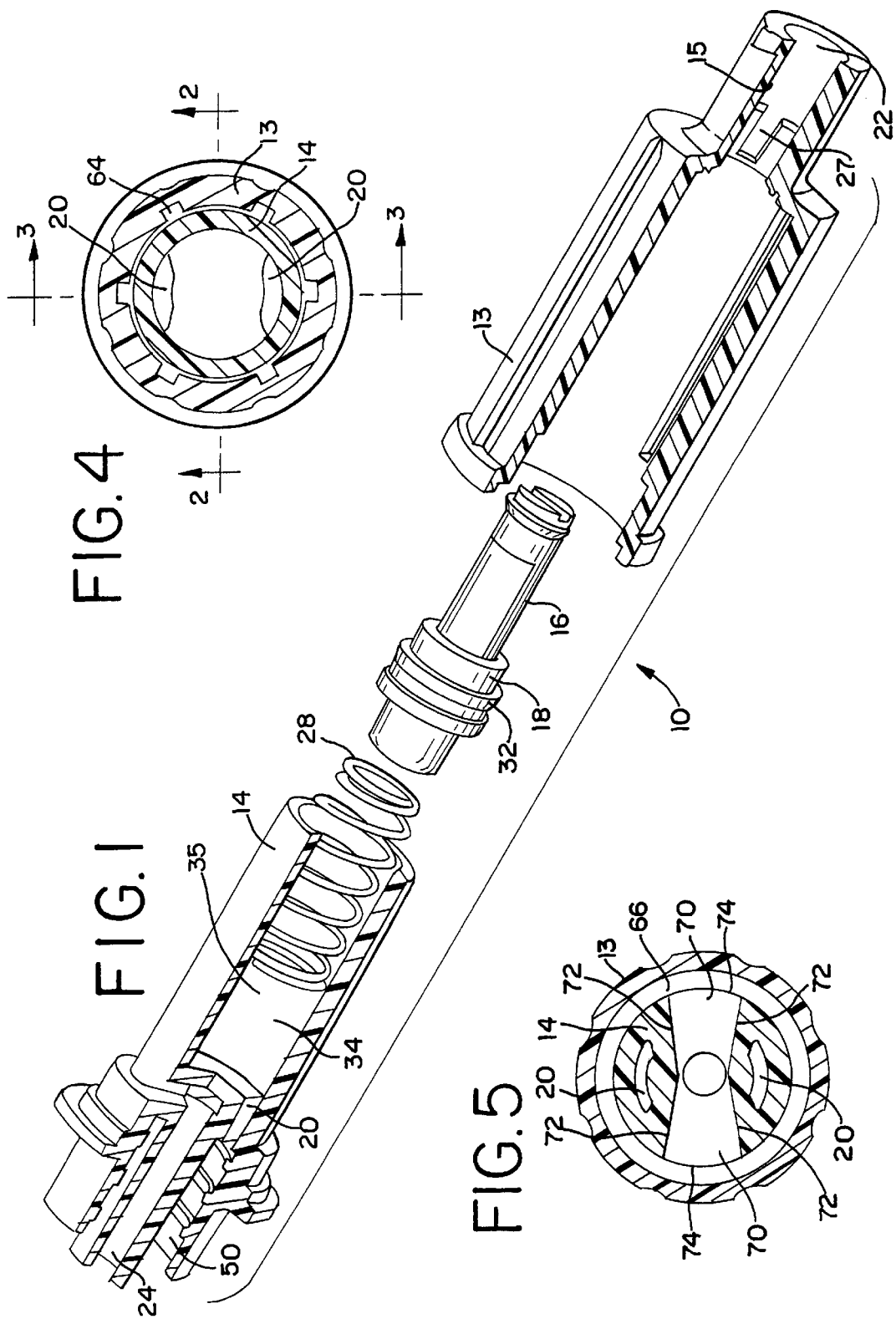
FIG. 1 is a perspective exploded view of a preferred embodiment of the present invention.

A preferred embodiment of the improved needleless access device 10 of the present invention is shown in FIGS. 1–7. The improved needleless access device 10 comprises a housing 12 made of a cap 13 and a body 14. The housing 12 has an inlet opening 22 and an outlet 24. Inside the top portion of the cap 13, beginning at the inlet opening 22, is a channel 15 forming a fluid passageway through the cap 13. The channel 15 is tapered so that the channel 15 and the inlet 22 form a standard female luer. The outlet 24 is a standard male luer.

Figure 7:
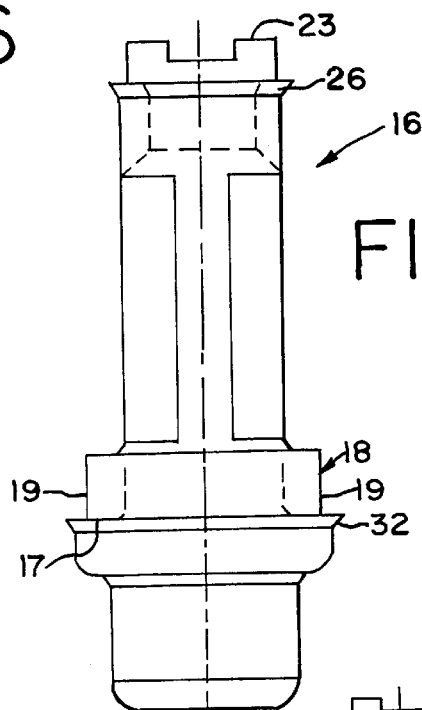
FIG. 7 is an elevational view of the plunger used in the needleless access device of FIGS. 2 and 3.

Referring to FIGS. 2, 3 and 7, a plunger 16 with an integrally molded seal 18 is biased upwardly by a spring 28. An inner chamber 34 is formed in the body 14 of the housing 12. A vent 20 leads from the inner chamber 34 through the body 14 portion of the housing 12 to the atmosphere. The vent 20 allows air to move into and come out of the inner chamber 34.

In a preferred embodiment the cap 13 is ultrasonically welded to the body 14. The cap 13 and the body 14 are preferably made of a rigid plastic such as Ektar, which is a Cole polyester material.

Referring to FIG. 7, the plunger 16 is generally cylindrical in shape. The diameter of the plunger 16 varies along its length. The proximal end of the plunger 16 is sized to fit the inside of the channel 15 that is disposed within the cap 13. The plunger 16 is preferably made of a rigid plastic such as polypropylene. A first wiper seal 26 is molded on the perimeter of the plunger 16 near its top end 23.

Referring again to FIG. 7, the bottom seal 18 is integrally formed on the plunger 16. The bottom seal 18 is generally cylindrical in shape. In a preferred embodiment the bottom seal 18 has a diameter of approximately 0.220 inches and a thickness of approximately 0.075 inches.

A main seal 32 is preferably formed just below the bottom seal 18. In a preferred embodiment, the main seal 32 is a wiper seal. In a preferred embodiment the diameter of the main seal 32 is approximately the same as the diameter of the inner chamber 34. The first wiper seal 26, the bottom seal 18 and the main seal 32 are preferably made of a thermoplastic elastomer, such as Sanoprene.

Referring to FIG. 3, a fluid pathway or channel 60 is shown and includes an upper space 62, mid-channels 64 and a lower channel 66. The upper space 62 is located just below the flow channels 27 and is generally cylindrical in shape. As shown in FIGS. 3 and 4, six mid-channels 64 are disposed below the upper space 62. The mid-channels 64 are in fluid communication with the upper space 62 and are generally rectangular shaped in cross section. As depicted in FIGS. 2 and 5, disposed below the mid-channels 64 is the lower channel 66. The lower channel 66 is in fluid communication with the mid-channels 64 and, like the upper space 62, is generally cylindrical in shape.

In a preferred embodiment, the upper space 62 has a diameter of approximately 0.375 inches and a width of 0.032 inches. The mid-channels 64 are preferably cut approximately 0.030 inches into the cap, and have a width or channel width of 0.050 inches. In a preferred embodiment, the lower channel 66 has a diameter of 0.435 inches and a width of 0.040 inches.

Referring to FIGS. 2 and 5, two conduits 70 are formed in the body 14. The conduits 70 are disposed between the lower channel 66 and an opening 25 of the outlet 24. Each conduit 70 preferably has two slanting sidewalls 72 and an open end 74. The conduits 70 form a fluid flow path from the channel 60 to the opening 25 of the outlet 24.

Referring to FIGS. 1 and 3, the outlet 24 is a cylindrical opening disposed in the lower portion of the body 14. The outlet 24 is generally cylindrical in shape. An opening 25 is located at the uppermost portion of the outlet 24. The opening is rectangular shaped in the cross section shown in FIG. 3.

The opening 25 receives fluid from the conduit 70 and passes it the outlet 24. The outlet 24 permits the fluid to flow out of the body 14 to its intended location, such as an IV line.

Referring to FIGS. 1 and 2, the inner chamber 34 is formed by a perimeter wall 35 in the body 14 portion of the housing 12. The inner chamber 34 has a top portion 36, a bottom portion 38 and a perimeter wall 35. The perimeter wall 35 is generally cylindrical in shape and has a tapered end portion 46. In a preferred embodiment the perimeter wall 35 is rigid.

The inner chamber 34 is designed to receive air that enters through the vent 20 after fluid is injected using the device 10.

In a preferred embodiment the diameter of the perimeter wall 35 is approximately 0.275 inches and the length of the perimeter wall 35 is 0.645 inches. The tapered end portion 46 preferably has a diameter of approximately 0.255 inches and a length of 0.075 inches.

As shown in FIGS. 1, 3 and 5, vents 20 are located between a bottom portion 48 of the end portion 46 of the inner chamber 34 and the open threaded exit portion 50 of the body 14. Referring to FIG. 5, the vents 20 are rectangular shaped in the cross section. In a preferred embodiment, the vents 20 are oriented parallel to the central axis 11. Alternatively, the vents 20 may be oriented at an acute, obtuse or a right angle with respect to the central axis. The vents 20 permit air to enter into and pass out of the inner chamber 34. In a preferred embodiment the vents 20 have a length of approximately 0.130 inches.

As best seen in FIGS. 2 and 3, the plunger 16 is in a first position. The first wiper seal 26 is at the top 23 of the cap 13 and acts to seal the top of the channel 15 and the inlet 22. When the plunger 16 is in the first position, the ends 19 of the bottom seal 18 abut the cap 13, thereby preventing fluid from the flow channels 27 from moving into the channel 60. Also, the main seal 32 abuts the perimeter wall 35 at the top 36 of the inner chamber 34 and thereby seals the inner chamber 34 from fluid that may be in the channel 60. When the plunger 16 is in this first position the inner chamber 34 is filled with air.

Figure 6:
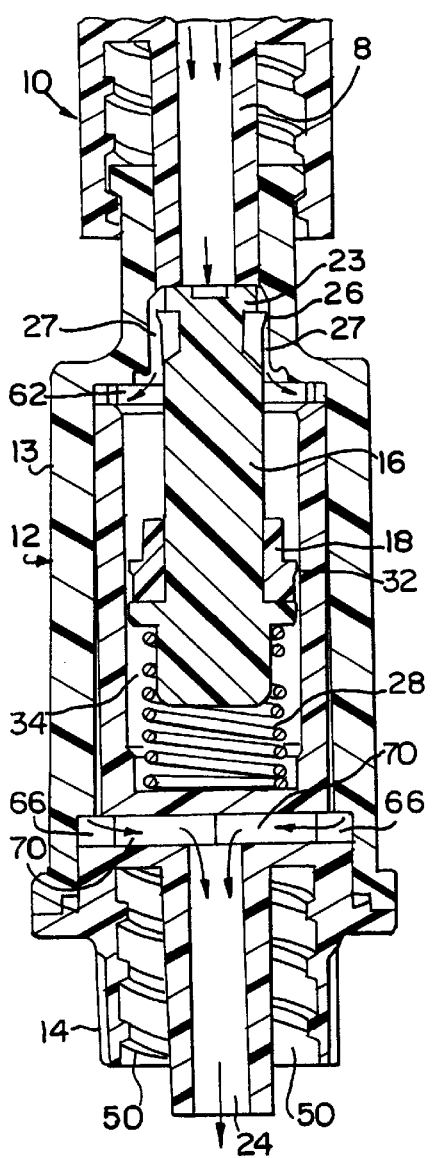
FIG. 6 is a cross-sectional view of the embodiment of the invention shown in FIGS. 2 and 3 when the plunger is in a second position.

As the tip of the syringe 8 is inserted into the inlet 22 and forced into the channel 15, the plunger 16 shifts downward toward a second position shown in FIG. 6. In this second position, the plunger 16 is depressed to a level such that the first wiper seal 26 is just below the tops of the flow channels 27 and the bottom seal 18 is within the inner chamber 34. As a result, fluid injected by the syringe 8 flows out the tip, over the top 23 of the plunger 16, through the flow channels 27 and into the channel 60.

The fluid flows from the upper space 62, to the mid-channels 64, and then to the lower channel 66. From the lower channel the fluid flows through the conduits 70 to the opening 25 and then finally out through the outlet 24. Fluid also fills the portion of the inner chamber 34 between the bottom seal 18 and the upper space 62.

As the syringe 8 and plunger 16 are shifted downward from the first position shown in FIGS. 2 and 3 to the second position shown in FIG. 6, the air contained within the inner chamber 34 is pushed out to the atmosphere through the vent 20.

Referring again to FIG. 6, when the syringe 8 is pulled out, the plunger 16 is biased in an upward direction by the spring 28 from the second position shown in FIG. 6 back to the first position shown in FIGS. 2 and 3. As the plunger shifts upward the fluid in the inner chamber 34 is pushed out of the inner chamber 34 through the channel 60. Also, as the plunger is shifted upward out of the inner chamber 34, air enters and fills the empty space in the inner chamber 34 through the vent 20. The air entering the inner chamber 34 prevents the reflux of fluid and blood that may otherwise have come back through the outlet 24 because of the empty space in the inner chamber 34. After the syringe 8 is removed, the plunger 16 returns to the first position shown in FIGS. 2 and 3.

Figure 8:
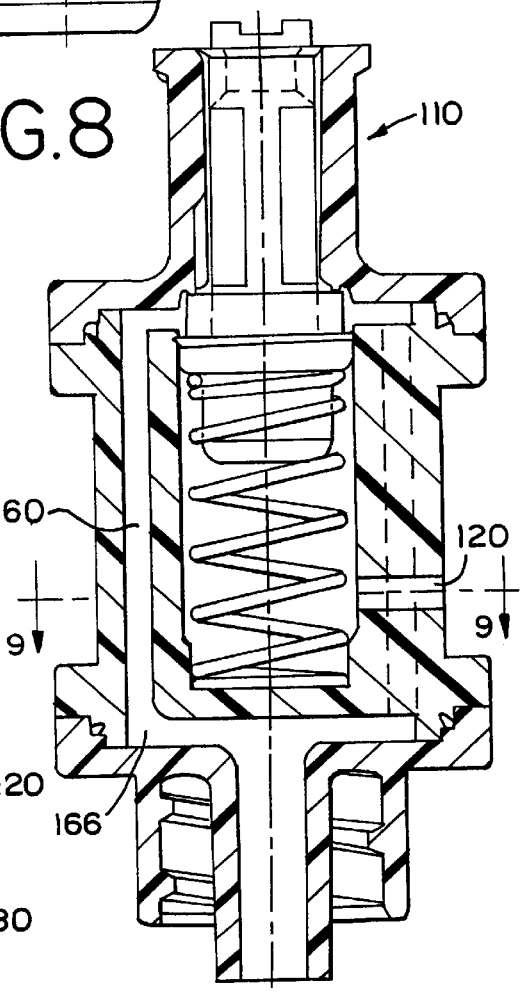
FIG. 8 is a cross-sectional view of a second embodiment of the present invention.
Figure 9:
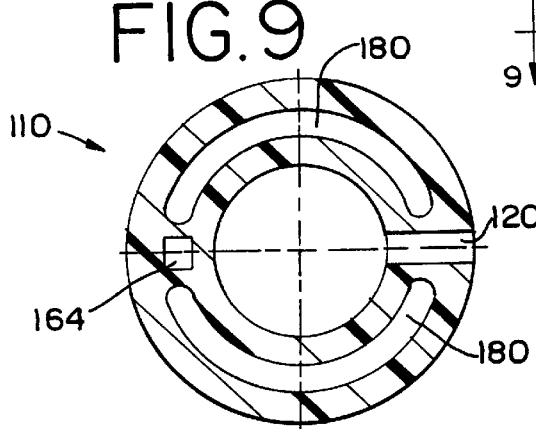
FIG. 9 is a cross-sectional view taken along line 9—9 of FIG. 8.

The second preferred embodiment of an improved needleless access device 110 of the present invention is shown in FIGS. 8 and 9. The device 110 is generally the same as the device 10 of FIGS. 1–6, and the similar elements have reference numbers that differ by an addend of 100. However, the exact same plunger 16 used in the first embodiment can be used in this second embodiment.

There are some differences between the first embodiment and the second embodiment. First, the second embodiment has a vent 20 that is aligned horizontally with respect to the inner chamber 134 or perpendicular with respect to the central axis 11, as opposed to the two vertical 20 vents of the first embodiment. Further, the second embodiment only has one mid-channel 164 that is rectangular shaped in the cross section, as shown in FIG. 9, and connects directly to the outlet 124 via a lower channel 166. In addition, as shown in FIG. 9, the second embodiment includes voids 180 that are formed in the body. The voids 180 are semicircular openings disposed in the body and are approximately the same length as the channel 160.

A third embodiment of the needleless access device 210 of the present invention is shown in FIG. 10. The device 210 is generally the same as device 10 of FIGS. 1–6, and the similar elements have reference numbers that differ by an addend of 200. The third embodiment, however, has one horizontally oriented vent 220 instead of two. In addition, the third embodiment has a cylindrical shaped mid-channel 264 that is formed between the cap 213 and the body 214. Further, the third embodiment has an opening 225 that is circular shaped in cross section.

A fourth embodiment of the needleless access device 310 of the present invention is shown in FIG. 11. The device 310 is generally the same as device 10 of FIGS. 1–6, and the similar elements have reference numbers that differ by an addend of 300. The fourth embodiment, however, has one vertically oriented vent 320. In addition, the fourth embodiment has a cylindrical shaped mid-channel 364 that is formed between the cap 313 and the body 314. Further, the fourth embodiment has an opening 325 that is circular shaped in cross section.

A fifth embodiment of the needleless access device 410 is shown in FIG. 12. The device 410 is generally the same as device 10 of FIGS. 1–3, and the similar elements have reference numbers that differ by an addend of 400. The fifth embodiment has a horizontal vent 420 as opposed to a vertical vent. In addition, the body 414 in the fifth embodiment has tabs 490, because the cap 413 is molded around the body 414 as opposed to ultrasonically welded. Further, the fifth embodiment has one semi-cylindrical mid channel 464 and a lower channel 466 that is directly connected to the outlet 424 as opposed to an opening.

A sixth embodiment of the needleless access device 510 is shown in FIG. 13. The device 510 is generally the same as the device 10 of FIGS. 1–6, and the similar elements have reference numbers that differ by an addend of 500. The sixth embodiment is similar to the fifth embodiment, however, it has one vertical vent 520 on the right side of the device 510 (as shown from the cross section in FIG. 13). The fifth embodiment also has tabs 590, because the cap 513 is molded around the body 514.

There are several embodiments of plungers that may be used with any one of the foregoing devices 10, 110, 210, 310, 410 and 510. These are shown in FIGS. 14–23.

Figure 14:
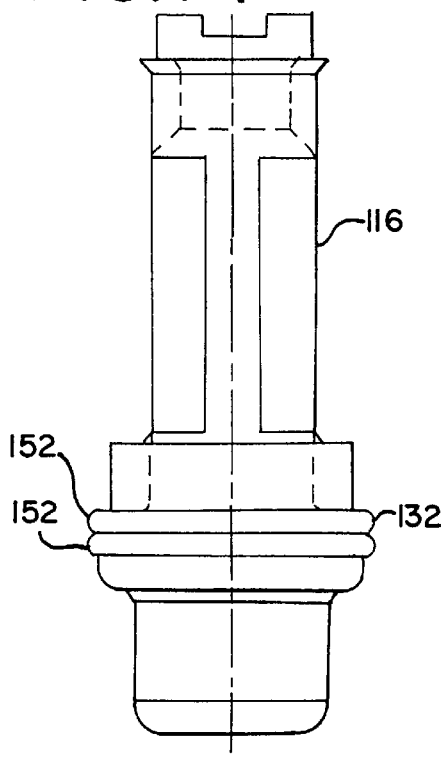
FIG. 14 is an elevational view of a second embodiment of a plunger for use in the present invention.

The second embodiment for a plunger for the present invention is shown in FIG. 14. The plunger 116 is generally the same as the plunger 16 for the device 10 of FIG. 7, and the similar elements have reference numbers that differ by an addend of 100. In the second embodiment of the plunger 116 the main seal 132, however, is comprised of molded rings 152 instead of a wiper seal 132.

Figure 15:
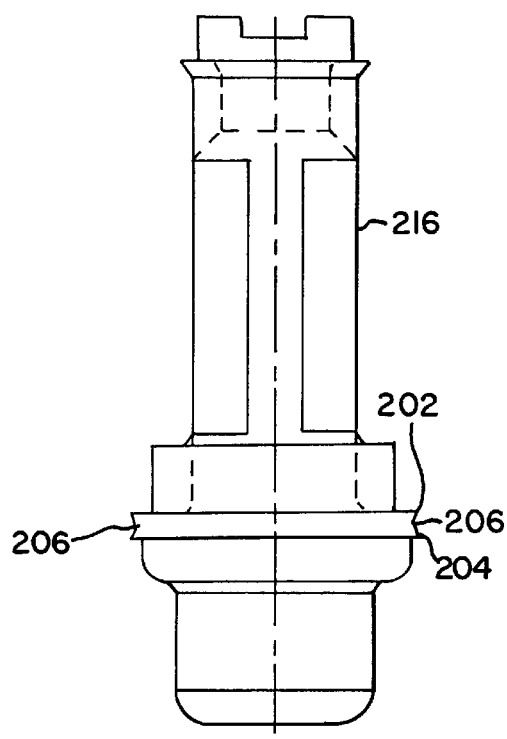
FIG. 15 is an elevational view of a third embodiment of a plunger for use in the present invention.

A third embodiment of the plunger 216 is shown in FIG. 15. The plunger 216 is generally the same as the plunger 16 of FIG. 7. Instead of a wiper seal, the plunger 216 in FIGS. 15–18 has a main seal that is concave shaped at the ends 206 and has a top edge 202 and a bottom edge 204 that, when the plunger 200 is inserted in the inner chamber 34, contact the perimeter wall 35.

Figure 16:
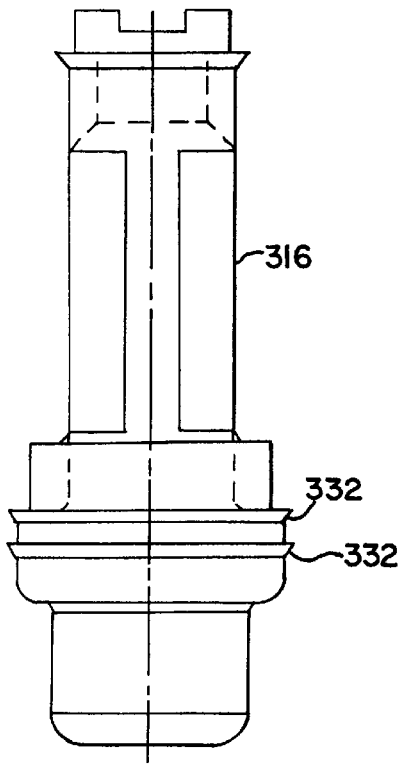
FIG. 16 is an elevational view of a fourth embodiment of a plunger for use in the present invention.

A fourth embodiment of the improved plunger 316 is shown in FIG. 16. The plunger 316 is generally the same as the plunger 16 of FIG. 7. The plunger 316 uses two wiper seals 332 instead of a single wiper seal as the main seal 332. Two wiper seals 332 may be more useful for high pressure applications.

Figure 17:
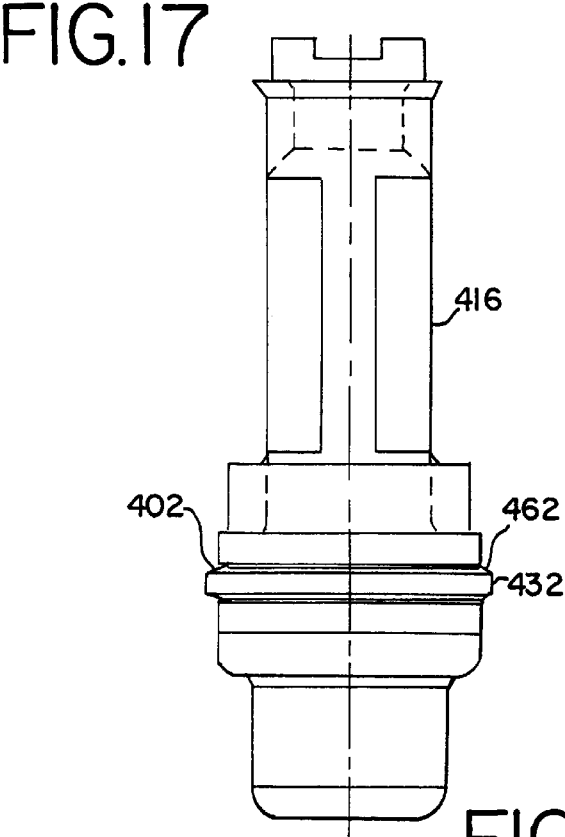
FIG. 17 is an elevational view of a fifth embodiment of a plunger for use in the present invention.

A fifth embodiment of the plunger 416 is shown in FIG. 17. The plunger 416 is generally the same as the plunger 16 of FIG. 7. The plunger 416 uses, however, a band seal as the main seal 432 instead of a wiper seal. The band seal 432 is generally cylindrical in shape and has tapered ends 406 that contact the perimeter wall of the inner chamber.

Figure 18:
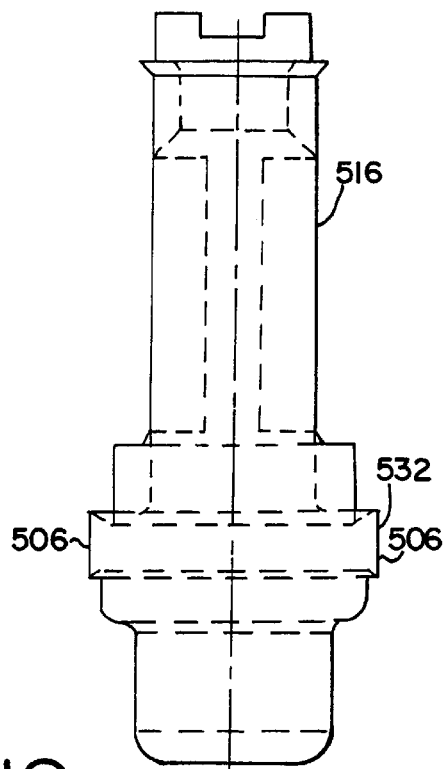
FIG. 18 is an elevational view of a sixth embodiment of a plunger for use in the present invention.

Referring to FIG. 18, a sixth embodiment of the plunger 516 is shown. Instead of a wiper seal that is shown in FIG. 7, this embodiment uses a main seal 532 that has ends 506 that are generally trapezoidal shaped in cross section.

Figure 19:
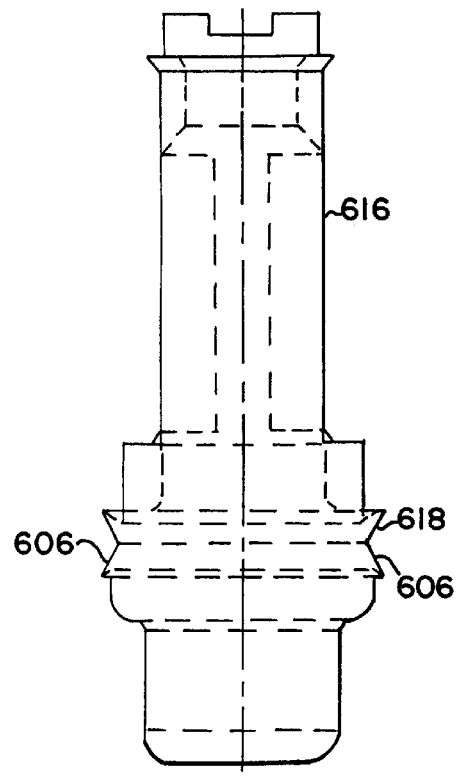
FIG. 19 is an elevational view of a seventh embodiment of a plunger for use in the present invention.

Referring to FIG. 19, a seventh embodiment of the plunger 616 is shown. The main seal 618 of this embodiment has triangular shaped ends 606.

Figure 20:
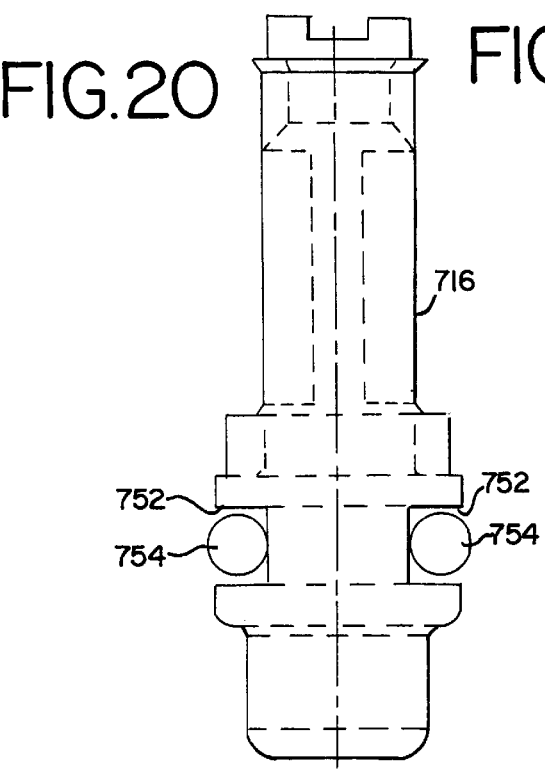
FIG. 20 is an elevational view of an eighth embodiment of a plunger for use in the present invention.

A seventh embodiment of the plunger 716 is shown in FIG. 20. Instead of a wiper seal 732, the plunger 716 in FIG. 20 has a groove 752. Disposed within the groove is an o-ring 754, that is circular shaped in cross section. When the plunger 716 is placed in the device 10, the o-ring 754 abuts the perimeter wall 35 of the inner chamber 34.

Figure 21:
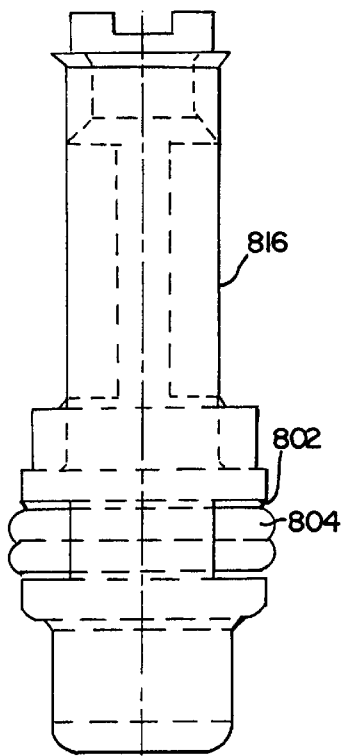
FIG. 21 is an elevational view of a ninth embodiment of the plunger for use in the present invention.

Referring to FIG. 21, an eighth embodiment of the plunger 816 is shown. The plunger 816 has a groove 802 and a sealing ring 804 that is elliptical shaped in cross section. When the plunger 816 is placed in the device 10 the sealing ring 804 abuts the perimeter wall 35 of the inner chamber 34.

Figure 22:
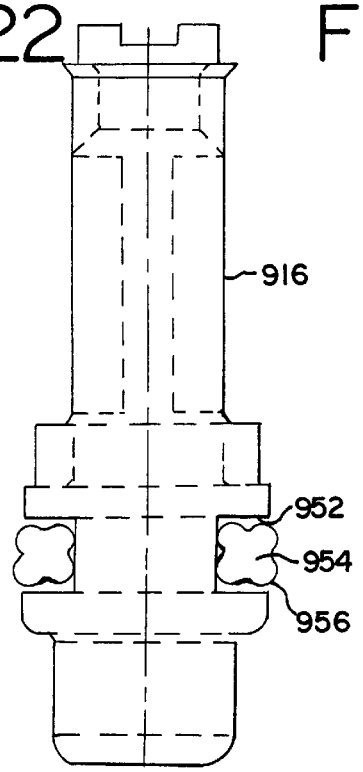
FIG. 22 is an elevational view of a tenth embodiment of a plunger for use in the present invention.

Referring to FIG. 22, a ninth embodiment of the plunger 916 is shown. This embodiment also has a groove 952 and main sealing ring 954. The cross-sectional shape of the sealing ring shown in FIG. 22 has a plurality of curved edges 956.

Figure 23:
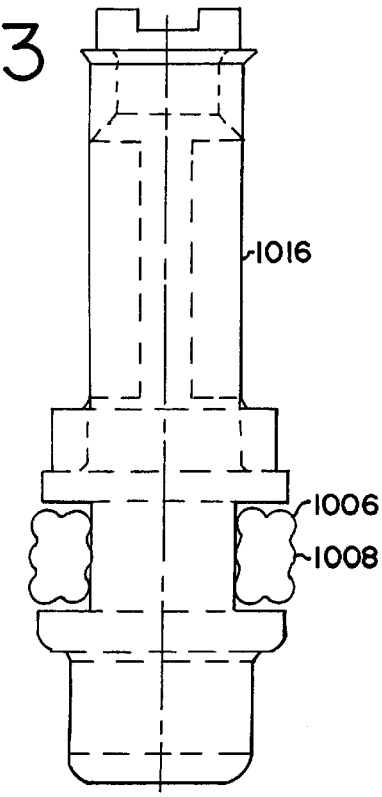
FIG. 23 is an elevational view of an eleventh embodiment of a plunger for use in the present invention.

The plunger 1016 shown in FIG. 23 is similar to the one in FIG. 22 and has a sealing ring 1006 that also has a cross-sectional shape which has a plurality of curved edges 1008.

The embodiments described above and shown herein are illustrative and not restrictive. The scope of the invention is indicated by the claims rather than by the foregoing description and attached drawings. The invention may be embodied in other specific forms without department from the spirit of the invention. Accordingly, these and any other changes which come within the scope of the claims are intended to be embraced therein.

What is claimed is:

1. A needleless access device comprising:
   (a) a housing comprising an interior wall and an exterior wall, said housing having:
      (i) a fluid pathway defined by at least one flow channel formed between said interior wall and said exterior wall; and
      (ii) an inner chamber formed within said interior wall;
   (b) a biased plunger disposed within said. inner chamber-movable between a first position and a second position;
   (c) a main seal sealing said inner chamber from said fluid pathway; and
   (d) a vent between said inner chamber and the outside of the housing to allow air to pass out of and into said inner chamber when said plunger is moved between said first and second positions.

2. The needleless access device of claim 1 wherein a stretchable element in said inner chamber biases said plunger towards said first position.

3. The needleless access device of claim 1 wherein said main seal is a wiper seal that is integrally molded as part of said plunger.

4. The needleless access device of claim 1 wherein said main seal slidably engages an interior surface on said interior wall.

5. The needleless access device of claim 1 wherein a bottom seal is integrally molded to said plunger and is positioned to seal said fluid pathway.

6. The needleless access device of claim 2 wherein said stretchable element is a spring.

7. The needleless access device of claim 1 wherein said inner chamber is defined in part by an interior surface of said interior wall.

8. The needleless access device of claim 7 wherein said interior wall is rigid.

9. The needleless access device of claim 7 wherein said interior wall has an annular cross-section.

10. The needleless access device of claim 1 wherein said inner chamber is generally cylindrical in shape.

11. The needleless access device of claim 1 wherein said flow channel comprises an upper space, a mid-channel and a lower channel.

12. The needleless access device of claim 11 wherein said mid-channel comprises a rectangular shaped cross-section.

13. The needleless access device of claim 1 wherein said housing further comprises an inlet opening and a first seal, wherein said first seal seals said fluid pathway from said inlet opening when said plunger is in said first position.

14. The needleless access device of claim 1 wherein air passes out of said inner chamber through said vent as said plunger moves from said first position to said second position and wherein air enters into said inner chamber through said vent as said plunger moves from said second position to said first position.

15. The needleless access device of claim 1 wherein said fluid pathway and said inner chamber are connected by a conduit.

16. The needleless access device of claim 1 wherein said vent is oriented parallel with respect to a central axis of said inner chamber.

17. The needleless access device of claim 1 wherein said vent is oriented perpendicular with respect to a central axis of said inner chamber.

18. A needleless access device comprising:
   (a) a housing comprising a cap and a body, said cap comprising an inlet and said body comprising an outlet, wherein an inner chamber is formed within an interior surface of said body and a fluid pathway is formed between said cap and an exterior surface of said body, said fluid pathway comprising an upper space, a mid-channel and a lower channel:
   (b) a biased plunger disposed within said inner chamber and movable between a first position and a second position, said biased plunger comprising a first seal that engages an interior surface of said cap and a main seal that engages said interior surface of said body, wherein said first seal seals said fluid pathway from said inlet when said plunger is in said first position and said main seal seals said inner chamber from said fluid pathway;
   (c) a vent through said housing and connected to said inner chamber to allow atmospheric air to pass out of and into said inner chamber when said plunger is moved between said first position and said second position.

19. The needleless access device of claim 18 wherein said main seal is a wiper seal.

20. A needleless access device comprising:
   (a) a rigid housing comprising an inlet portion having an inlet opening, an outlet portion having an outlet opening, an interior wall, and an exterior wall generally disposed about said interior wall, wherein an inner chamber is formed within an interior surface of said interior wall and a fluid pathway is formed substantially between an exterior surface of said interior wall and an interior surface of said exterior wall, said fluid pathway comprising an upper space, a mid-channel and a lower channel, said lower channel in fluid communication with said outlet opening;
   (b) a substantially rigid plunger generally disposed within said inner chamber and movable between a first position and a second position, said plunger being biased in said first position by a spring disposed within said inner chamber, said plunger comprising a first seal that engages an interior surface of said inlet portion and a main seal that slidably engages said interior surface of said interior wall, wherein said first seal seals said fluid pathway from said inlet opening when said plunger is in said first position, and further wherein said main seal seals said inner chamber from said fluid pathway;
   (c) a vent through said housing and connected to said inner chamber to allow air to pass out of and into said inner chamber when said plunger is moved between said first position and said second position.

\* \* \* \* \*

UNITED STATES PATENT AND TRADEMARK OFFICE
CERTIFICATE OF CORRECTION

PATENT NO.     : 6,228,069 B1
DATED          : May 8, 2001
INVENTOR(S)    : Steve C. Barth et al.

It is certified that error appears in the above-identified patent and that said Letters Patent is hereby corrected as shown below:

Claim 1,
Line 8, delete "." immediately after "said"; delete "-" after "chamber".

Claim 18,
Line 2, insert -- rigid -- before "housing".
Line 8, delete ":" and substitute -- ; -- in its place.

Signed and Sealed this

Second Day of April, 2002

*Attest:*

JAMES E. ROGAN
*Attesting Officer*  *Director of the United States Patent and Trademark Office*